United States Patent
Senn et al.

Patent Number: 6,095,812
Date of Patent: Aug. 1, 2000

[54] DEVICE FOR CURING WITH LIGHT

[75] Inventors: Bruno Senn, Buchs; Gregor Fritsche; Gottfried Rohner, both of Altstätten, all of Switzerland

[73] Assignee: Ivoclar AG, Schaan, Liechtenstein

[21] Appl. No.: 09/260,318

[22] Filed: Mar. 1, 1999

Related U.S. Application Data

[60] Provisional application No. 60/084,214, May 5, 1998.

[30] Foreign Application Priority Data

Mar. 11, 1998 [DE] Germany .............................. 198 10 573

[51] Int. Cl.$^7$ ........................................................ A61C 1/00
[52] U.S. Cl. .................................................................. 433/29
[58] Field of Search .......................... 433/28, 29; 362/183, 362/804

[56] References Cited

U.S. PATENT DOCUMENTS

| | | | |
|---|---|---|---|
| 4,450,139 | 5/1984 | Bussiere et al. | 433/29 |
| 5,267,857 | 12/1993 | Sickler | 433/29 |
| 5,471,129 | 11/1995 | Mann . | |
| 5,530,632 | 6/1996 | Shikano et al. | 433/29 X |
| 5,879,159 | 3/1999 | Cipolla | 433/29 |

FOREIGN PATENT DOCUMENTS

| | | |
|---|---|---|
| 0166364 A2 | 1/1986 | European Pat. Off. . |
| 0508526 A1 | 10/1992 | European Pat. Off. . |
| 3605278 C1 | 2/1986 | Germany . |
| 09069395 | 3/1997 | Japan . |
| WO 90/01247 | 2/1990 | WIPO . |

*Primary Examiner*—Nicholas D. Lucchesi
*Attorney, Agent, or Firm*—John C. Thompson; Alan S. Korman

[57] ABSTRACT

A curing device for curing dental materials by light-induced polymerization has a supply station and a hand-held apparatus including a light source. A detachable cable connects the hand-held apparatus to the supply station. An output control device controls the light source in order to ensure a uniform light intensity, wherein the output control device has a preset nominal output. The output control device includes a control FET. The cable is connected within the output control device. The output control device prevents switching on the curing device or emits a warning signal when the nominal output requires a voltage, surpassing a control bias voltage minus a potential difference of the control FET, or a corresponding current.

15 Claims, 3 Drawing Sheets

DEVICE FOR CURING WITH LIGHT

This application is a continuation of provisional application 60/084,214 filed May 5, 1998.

BACKGROUND OF THE INVENTION

The present invention relates to a curing device employing light, especially for the polymerization of dental materials by light, comprising a hand-held device with light source that is connected by a cable to a supply station whereby the cable is detachable and can be plugged into the hand-held apparatus and the supply station. A control unit for the light source is provided in order to ensure a uniform light emission or intensity.

Various curing devices for curing by light are known which are mains-powered and which are used for the light-induced polymerization of dental materials. A hand-held apparatus receives the light source and connected by a cable to the supply station. Such curing devices have the advantage, in comparison to battery-operated curing devices, that a higher light output can be provided and that the hand-held apparatus itself is light-weight since the weight of the battery or accumulator has been eliminated.

In known curing devices the supply voltage for the light source in the supply station is stabilized in a manner known per se by a voltage controller. In these curing devices it is assumed that a voltage stabilization over the service life of the light source is sufficient in order to provide to sufficient light output for polymerization. In addition, it has been known to measure the light output of the hand-held apparatus whereby one example for such a light-curing device is known from German Gebrauchsmuster 92 12 892. In this curing device the supply station is provided with a light sensor which responds when the detected light is of sufficient intensity.

This solution however is disadvantageous because the action of monitoring whether the curing device still functions reliably is in the hands of the operator. Accordingly, different levels of responsibility on the user's part thus has a strong effect on the reliability of the device so that the manufacturers of such devices recommend to exchange the light source or lamp as a matter of precaution after about 100 hours of operating time.

Light sources which, for example, may be in the form halogen lamps are disposable items, However, there are considerable quality differences and thus differences in their service life. For example, for the same operating parameters, a lamp with a high-quality coil which is comprised of wire that is of uniform thickness and uniform roundness, may last three times longer than a light source of lower quality. However, whereby in known devices the improved service life of such high-quality light sources, which have also essentially a well defined spectrum, cannot be fully used for the aforementioned reasons.

A further disadvantage of such light curing devices is that they can be adapted only with difficulty to the local particularities of respective dental practices. While in some practices it is more favorable to arrange the supply station directly adjacent to the hand-held apparatus, such that a short cable is sufficient, in other practices the local particularities are such that an arrangement of supply station and of the hand-held apparatus spaced far apart is necessary.

These requirements of dental practices can be taken into consideration with known light curing devices only to a limited extent. The length of the cable may not surpass a certain limit in order not to impede the light intensity to be provided. On the other hand, the cable should not be too thick in order to provide the desired flexibility and bending ability so that in the past relatively limited minimum and maximum cable lengths have been provided. Furthermore, when supplying such curing devices, it must be specified which length of cable is desired in order to be able to adapt the light source control to the cable length. This must be performed by the manufacturer so that when the special requirements within the dental practice change or when it is determined that the initially ordered cable length is not sufficient, a complicated exchange with manipulations of the device by a service technician must be performed.

It is therefore an object of the present invention to provide a curing device of the aforementioned kind with improved economic use and greater flexibility with respect to its use.

SUMMARY OF THE INVENTION

A curing device for curing dental materials by light-induced polymerization is primarily characterized by:

a supply station;

a hand-held apparatus comprising a light source;

a detachable cable connecting the hand-held apparatus to the supply station;

an output control device controlling the light source in order to ensure a uniform light intensity, wherein the output control device has a preset nominal output;

the output control device comprising a control FET;

the cable connected within the output control device;

wherein the output control device prevents switching on the curing device or emits a warning signal when the nominal output requires a voltage, surpassing a control bias voltage minus a potential difference of the control FET, or a corresponding current.

Advantageously, the cable comprises a control line. The output control device preferably has a voltage sensor for detecting a terminal voltage of the light source and producing a terminal voltage signal. The output control device also may comprise a current sensor for detecting a current of the light source and producing a current signal. The output control device further includes an evaluation circuit. The terminal voltage signal and the current signal are supplied via the evaluation circuit to the control line of the cable.

Preferably, the cable comprises a control line and the supply station comprises a control circuit embodied as a switch control for controlling the control FET. The control circuit is preferably connected to the control line.

Expediently, the hand-held apparatus comprises a calibrating unit for calibrating the current sensor, the voltage sensor, and the evaluation circuit.

The evaluation circuit preferably comprises a dc/ac converter calibrated by the calibrating unit.

The hand-held apparatus has preferably a start/stop switch connected to the evaluation circuit, wherein the start/stop switch has a keying function and, when actuated, delivers a start signal to a control line.

Preferably, the control circuit has a control characteristic line for linearly increasing with increasing control voltage the output voltage beginning at a soft start value, wherein the output voltage is supplied through the cable to the light source.

Advantageously, the slope of the control function of the control circuit for controlling the control FET is slightly greater than 1.

The output control device preferably compensates for different lengths of the cable.

Advantageously, the hand-held apparatus includes a fan and auxiliary devices. The control FET supplies a controlled output voltage to the cable, and the fan and auxiliary devices are supplied by the cable with an auxiliary output voltage that is independent of the controlled output voltage.

The evaluation circuit has an output terminal for the fan for activating the fan, wherein the activation period of the fan for cooling the light source is determined by the evaluation circuit based on continuous or accumulated period of use of the light source.

The calibrating unit during calibration evaluates all components of the hand-held apparatus that exhibit tolerances. The calibrating unit includes a memory and the calibrating data are stored in the memory. The hand-held apparatus is calibratable independent of the length of the cable.

Preferably, the memory is in EEPROM, i.e., an electronically erasable programmable read only memory device.

Preferably, the evaluation circuit comprises a signal device for indicating that a lamp of the light source must be exchanged when the inner resistance of the light source is outside of a threshold value.

The threshold value is advantageously the controlled output voltage defined as the control bias voltage plus a minimum potential difference of the control FET.

Surprisingly, the inventive curing device provides a substantially improved use of the light source so that it is recommended to employ high-quality light sources having an extended service life so that the maintenance intervals for the light curing device can be extended substantially, for example, tripled. The inventive output control can be employed especially advantageously when inventively a voltage adjustment according to the inner resistance of the light source is provided.

The increase of the inner resistance is automatically monitored whereby according to a preferred embodiment a signal is emitted when the voltage adjustment no longer can provide a voltage corresponding to the inner resistance which means that the light source or lamp should be exchanged. The required nominal output in this case can no longer be ensured. This embodiment allows with especially simple but especially effective means a service life monitoring action which is adapted to the changes of the tungsten coils so that a portion of the service life of the light source is no longer wasted.

By including the cable it is not only possible to provide for a more precise stabilization of the light output but it is also no longer necessary to call a technician in order to adapt the light curing device to the desired cable length. The output control detects directly the voltage and current at the light source, i.e., its operating parameters, and then adjusts within the supply station that includes the control member the curing device components relative to one another. For this purpose, the cable contains an additional control line which may be very thin and which therefore does not impede the flexibility of the cable. Inventively, it is especially favorable that a cable that is comparatively thin and thus very flexible is employed because its inner resistance can be fully controlled.

According to an especially advantageous embodiment it is suggested that the cable is detachable and can be plugged into the hand-held apparatus and the supply station so that the dentist or the dental assistant can perform an adaptation of the light curing device to the desired cable length. Such cables can be ready made whereby employing standardized plugs and sockets make it possible to use pre-manufactured cables which are inexpensive.

In a preferred embodiment it is suggested to provide a second controlled auxiliary supply voltage that is independent of the controlled output voltage for supplying the lamp. The auxiliary supply voltage supplies auxiliary elements such as a fan etc. and is transmitted via a supply voltage line provided in the cable.

With such an independent auxiliary supply voltage line an improvement of the linear character of the control characteristic line for the output voltage, i.e., for supplying the light source, can be achieved whereby moreover the action of switching on the auxiliary elements will not disrupt the control circuit.

BRIEF DESCRIPTION OF THE DRAWINGS

The object and advantages of the present invention will appear more clearly from the following specification in conjunction with the accompanying drawings, in which.

DESCRIPTION OF PREFERRED EMBODIMENTS

The present invention will now be described in detail with the aid of several specific embodiments utilizing FIGS. 1 through 3.

Figure 1:
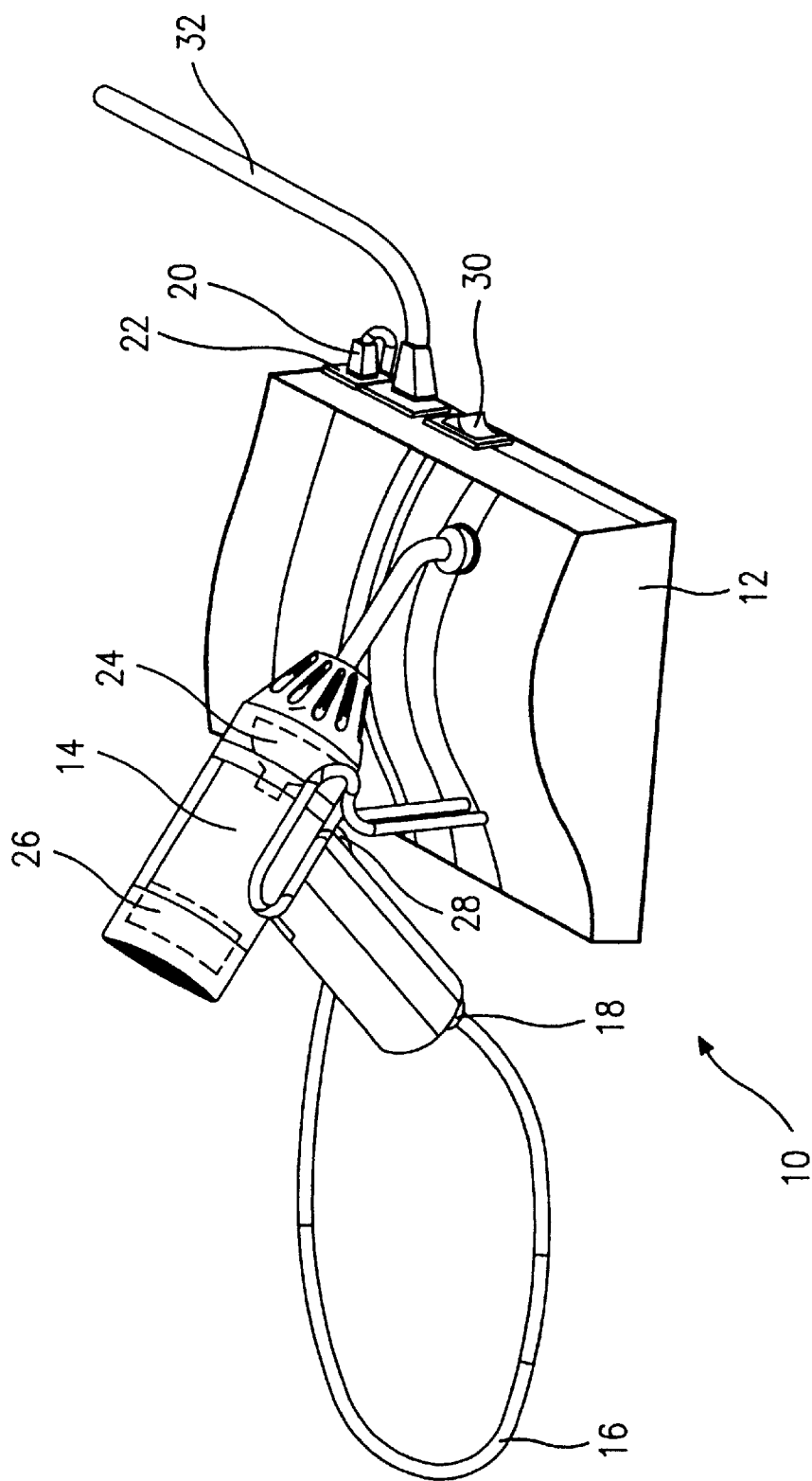
FIG. 1 is a perspective view of the inventive light curing device in one embodiment.

The light curing device represented in FIG. 1 comprises a supply station 12 and a hand-held apparatus 14 connected to one another by a cable 16. The cable 16 is provided at its end with plugs 18 and 20 which are received in respective sockets in the hand-held apparatus 14 and the supply station 12. The socket 22 at the supply station 12 can be seen in FIG. 1, and is represented schematically in FIG. 2.

The cable 16 is a multi-wire and highly flexible cable, and, as shown in FIG. 1, is relatively thin. Its weight therefore does not imped manipulation of the hand-held apparatus 14. Conventional cables used for such devices, on the other hand, have for a comparatively great flexibility, due to the used amount of copper, a relatively great weight.

The hand-held apparatus 14 is essentially pistol-shaped and contains a light source 24 and a fan 26 which are shown in a dashed tine. Also, a start/stop switch is provided whereby only the button 28 is shown in FIG. 1.

Figure 2:
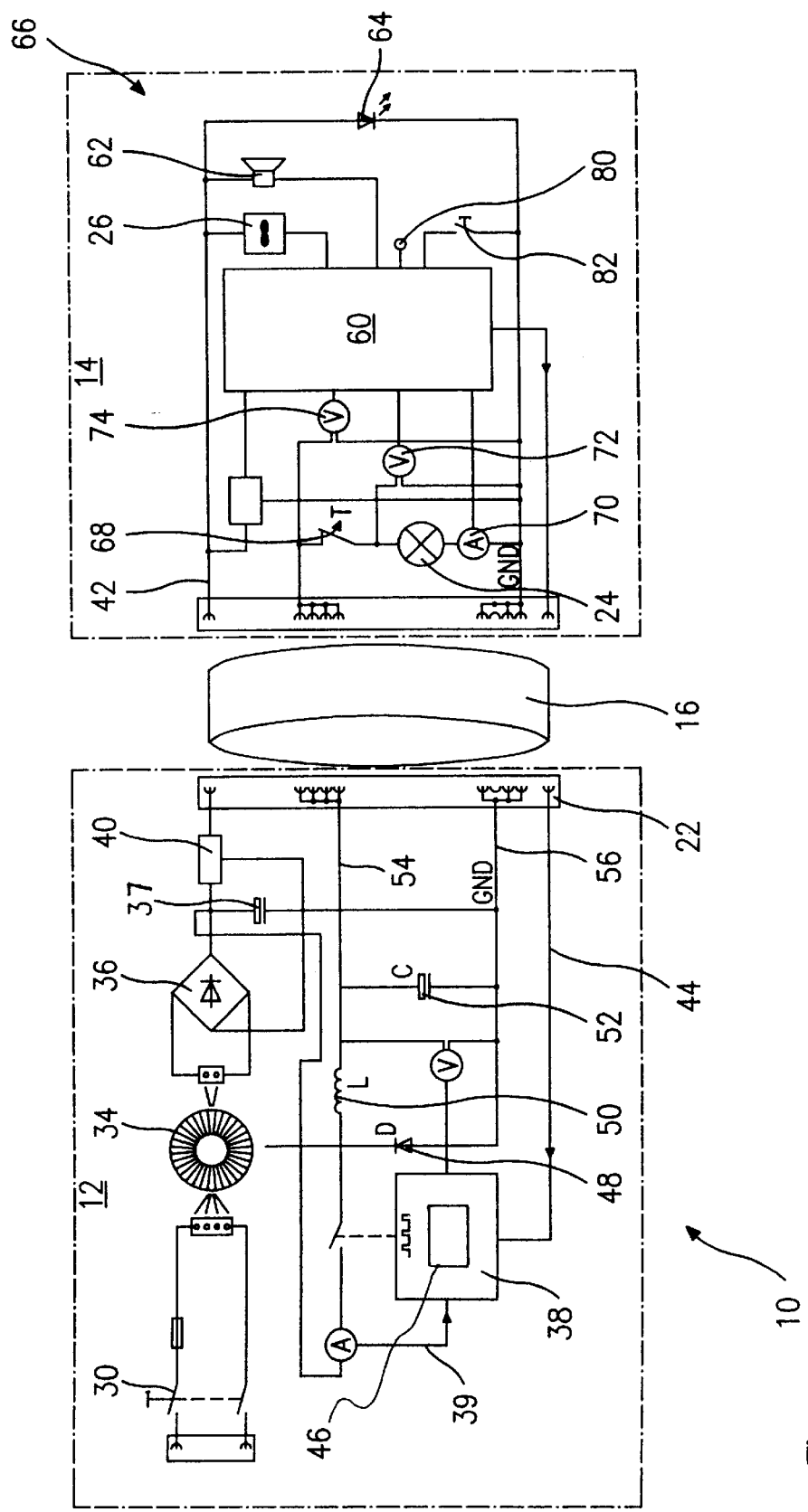
FIG. 2 is a circuit diagram for representing the electrical design of the light curing device in the embodiment according to FIG. 1.
Figure 3:
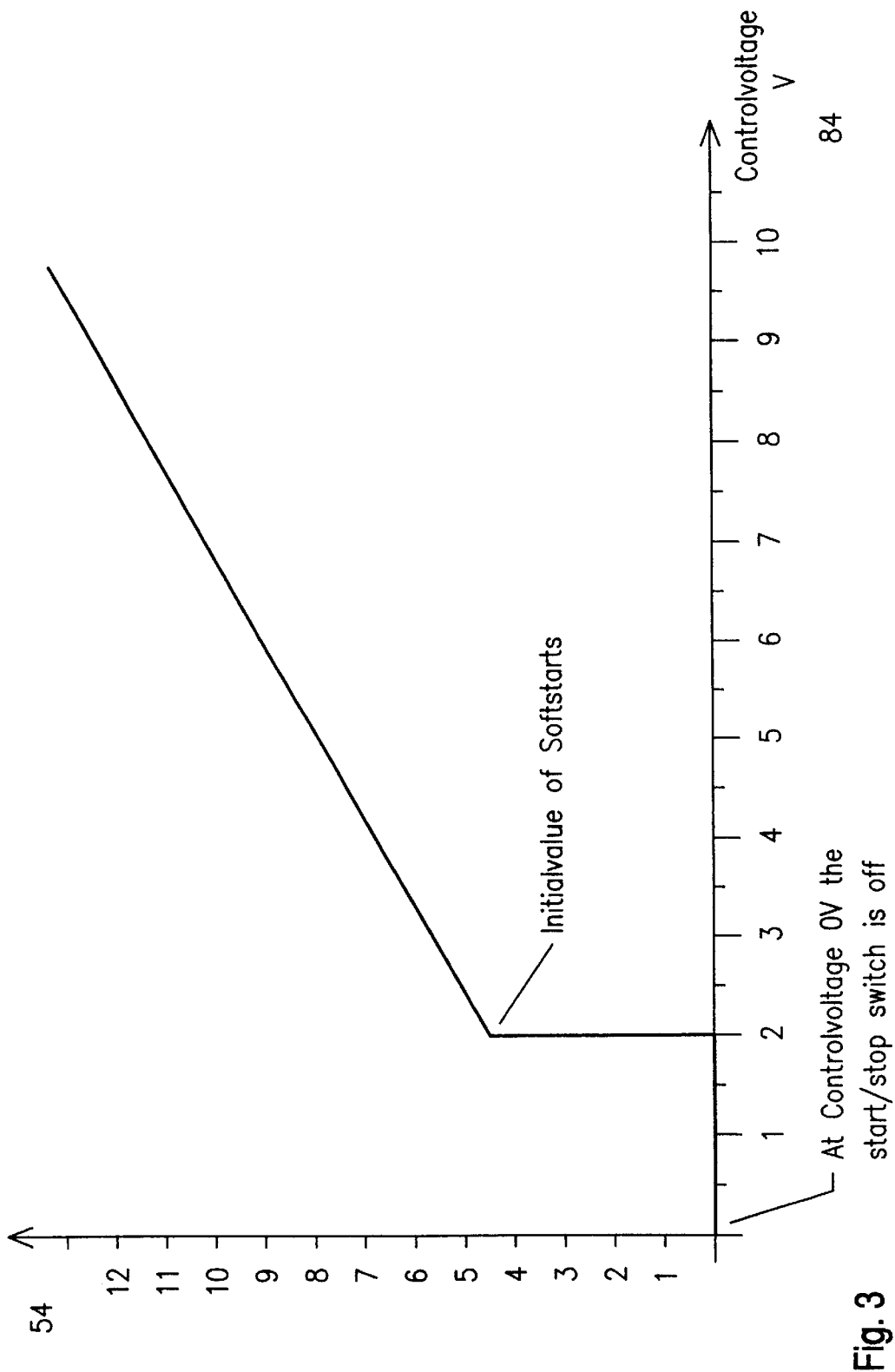
FIG. 3 shows the characteristic line for representing the soft start for the inventive light curing device.

FIG. 2 shows the circuit diagram of the inventive light curing device 10. The supply station 12 has, in a manner known per se, an on/off switch 30 which is supplied with electricity from the main cable 32. The main voltage is transformed to a secondary voltage by an annular transformer 34 and is then rectified by rectifier 36 and smoothed by a capacitor 37. The smoothed voltage at the output terminal of the rectifier 36 is the input voltage, which is referred to as the control bias voltage 39, used for the control circuit 38, to be described in more detail in the following, as well as for a fixed voltage controller 40 which provides the auxiliary supply voltage 42 transmitted via cable 16 to the hand-held apparatus 14.

The control circuit 38 comprises a control switch which is connected to the control bias voltage 39 and switches in response to an analog control signal, coming from the control line 44 extending through the cable 16, the control element 46. With this type of control a loss-reduced supply may be ensured while, in principle, it is also possible to use instead of the switching control a simple longitudinal control. The control element 46 is preferably a field effect transistor FET which is connected to the control bias voltage 39. The output voltage 54 of the control element 46 includes, in a manner known per se, an impulse-pause ratio depending on the control requirements so that substantially a rectangular or trapezoidal voltage is provided. When switched on, this output voltage corresponds to the control bias voltage 39 minus the potential difference of the FET 46. A negative preshooting of the switching peaks can be avoided by diode 48 whereby it is understood that with a corresponding diode connected to the input voltage 39 a positive overshooting can be avoided if needed. The output current of the control element 46 is smoothed by a coil 50 and further smoothed by a filter capacitor or smoothing capacitor 52 to such an extent that the output voltage 54 with a required minimal wave shape is provided and supplied to the cable 16.

In addition to the inventive control circuit it is suggested to provide a second output control circuit directly adjacent to the switching control 38. With this control circuit the input current of the line supplying the control voltage as well as the output voltage of the control element 46 are detected and also employed for the control action.

The cable 16 in the shown embodiment includes ten wires. However, it would be sufficient to have only four wires. One wire is designed for transmitting the auxiliary voltage 42. A further wire is provided as a control line 44. The remaining wires are divided onto the contacts for the output voltage 54 and for ground 56 whereby in the shown embodiment respectively four wires are used for these lines. It is understood that an adaptation within wide specification ranges is possible in this context. If needed, the cable 16 at the side connected to the hand-held apparatus may be provided with a further filter capacitor between the output voltage 54 and ground 56 whereby the inner resistance of the cable 16 further improves the smoothing of the output voltage.

The hand-held apparatus 14 employs the auxiliary supply voltage 42 for supplying voltage to an evaluation circuit 60, for the supply of the fan 26, for supplying a signal device 62 which may be embodied as a piezo buzzer as well as for supplying the operating display LED 64. These auxiliary elements 66 are thus taken out of the control circuit and therefore do not impede its linear action.

The light source 24 is connected via thermoswitch 68, which is a safety element, and via a current sensor 70 to the output voltage 54 and ground 56 at the secondary side of the cable 16, i.e., at the hand-held apparatus 42. The current sensor 70 comprises a current measuring resistor with a resistor value which is matched to the predetermined lamp power. For example, when the lamp has a power of 75 watt, the resistance of the current sensor 70 may be 0.025 ohm. The voltage potential generated by the light source current across the measuring resistor is detected by the current sensor 70 and supplied to the evaluation circuit 60.

Furthermore, a voltage sensor 72 is provided which detects the terminal voltage of the light source 24 as well as a further voltage sensor 74 which is directly connected to the output voltage 54 so that the evaluation circuit 60 can also detect activation of the thermoswitch 68 due to a difference of the output signal of the voltage sensors 72 and 74.

The evaluation circuit 60 provides a multiplication product of the detected voltage and current values of the sensor 70 and 72 and is connected to the control line 44 which is supplied with respective initial signals so that the control circuit 38 in the supply station 12 can provide a control of the output voltage 54 according to the respective power output nominal value of the evaluation circuit 60.

Furthermore, a calibration device is provided. The calibration device 80 comprises a start contact for compensation in which the exact magnitude of the measuring resistance of the current sensor 70 but also the linear function of the dc/ac convertor in the evaluation device 60 is memorized. The calibration device 80 comprises furthermore an EEPROM that is contained within the evaluation circuit 60 and has stored therein the respective calibration curve. Calibration can be performed for the entire hand-held apparatus 14 so that it is independent of the type and length of the cable 16 being used.

The light curing device can be started and stopped by a start/stop key 82 whereby the key 82 is actuated by the on/off switch 28. It is understood that the type of detecting of the relevant voltage and current values can be adjusted within wide ranges of respective specifications. For example, it is possible to employ a pure analog control of the evaluation circuit 60 which provides for a continuous voltage adjustment. However, a less expensive and more flexible digital control is sufficient whereby the speed requirements with respect to the digital/analog convertor are limited since, for example, a voltage adjustment can be performed within intervals of 100 msec.

Inventively, it is especially advantageous when via the start/stop key 82 is so-called soft start is realized. According to FIG. 3, when activating the on/off switch 28 predetermined voltage curve can be realized within the evaluation circuit 60 which allows for an increase of the output voltage 54 within, for example, 3 seconds. In FIG. 3 the output voltage 54 is represented as a function of the control voltage 84 which is present at the control line 44. It is shown that the slope is slightly more than 1 beginning at a threshold value of 2 Volt. Below a control voltage of 2 Volt the control circuit 38 is turned off so that for the start/stop key 82 in its turned off position no leak current flows through the light source 24.

Inventively, current and voltage can be simultaneously measured whereby a measuring event is performed within a spacing of a few nanoseconds. Preferably, measurement is performed at uniform intervals whereby the interval length is determined by the changing time of the digital/analog convertor. It is also possible to switch the input terminal of the convertor between current and voltage measurement so that only one convertor is needed.

What is claimed is:

1. A curing device for curing dental materials by light-induced polymerization, said curing device comprising:

a supply station;

a hand-held apparatus comprising a light source;

a detachable cable connecting said hand-held apparatus to said supply station; and an output control device controlling said light source in order to ensure a uniform light intensity, wherein the output control device has a preset nominal output, the output control device comprising a control FET; said cable connected within said output control device, wherein said output control device prevents switching on of the curing device, or emits a warning signal, when said nominal output requires a voltage, surpassing a control bias voltage minus a potential difference of said control FET, or a corresponding current.

2. A curing device according to claim 1, wherein:

said cable comprises a control line;

said output control device comprises a voltage sensor for detecting a terminal voltage of said light source and producing a terminal voltage signal;

said output control device further comprises a current sensor for detecting a current of said light source and producing a current signal;

said output control device further comprises an evaluation circuit;

said terminal voltage signal and said current signal supplied via said evaluation circuit to said control line of said cable.

3. A curing device according to claim 2, wherein:

said cable comprises a control line;

said supply station comprises a control circuit embodied as a switch control for controlling said control FET;

said control circuit connected to said control line.

4. A curing device according to claim 3, wherein said control circuit has a control characteristic line for linearly increasing with increasing control voltage an output voltage beginning at a soft start value, wherein the output voltage is supplied through said cable to said light source.

5. A curing device according to claim 4, wherein a slope of a control function of said control circuit for controlling said control FET is slightly greater than 1.

6. A curing device according to claim 2, wherein said hand-held apparatus comprises a calibrating unit for calibrating said current sensor, said voltage sensor, and said evaluation circuit.

7. A curing device according to claim 6, wherein said evaluation circuit comprises a dc/ac converter calibrated by said calibrating unit.

8. A curing device according to claim 6, wherein said calibrating unit during calibration evaluates all components of said hand-held apparatus that exhibit tolerances, wherein said calibrating unit comprises a memory and wherein calibrating data are stored in said memory, wherein said hand-held apparatus is calibratable independent of a length of said cable.

9. A curing device according to claim 8, wherein said memory is an EEPROM.

10. A curing device according to claim 2, wherein said hand-held apparatus has a start/stop switch connected to said evaluation circuit, wherein said start/stop switch has a keying function and, when actuated, delivers a soft start signal to a control line.

11. A curing device according to claim 2, wherein said output control device compensates for different lengths of said cable.

12. A curing device according to claim 2, wherein said hand-held apparatus comprises a fan and auxiliary devices, wherein said control FET supplies a controlled output voltage to said cable, and wherein said fan and said auxiliary devices are supplied via said cable with an auxiliary output voltage that is independent of said controlled output voltage.

13. A curing device according to claim 12, wherein said evaluation circuit has an output terminal for said fan for activating said fan, wherein an activation period of said fan for cooling said light source is determined by said evaluation circuit based on continuous or accumulated period of use of said light source.

14. A curing device according to claim 2, wherein said evaluation circuit comprises a signaling device for indicating that a lamp of said light source must be exchanged when an inner resistance of said light source is outside of a threshold value.

15. A curing device according to claim 14, wherein said threshold value is a controlled output voltage defined as said control bias voltage plus a minimum potential difference of said control FET.

* * * * *